United States Patent
Himmelsbach et al.

(10) Patent No.: US 6,858,110 B1
(45) Date of Patent: Feb. 22, 2005

(54) PARTIALLY SELF-ADHESIVELY TREATED ARTICLE WITH PERMANENTLY DEFORMED SELF-ADHESIVE COMPOSITION

(75) Inventors: Peter Himmelsbach, Buxtehude (DE); Peter Jauchen, Hamburg (DE); Klaus Keite-Telgenbüscher, Hamburg (DE); Matthias Lehder, Buchholz (DE); Reiner Leutz, Reinbek (DE); Jens Schreiber, Lüneburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/719,319

(22) PCT Filed: Jun. 8, 1999

(86) PCT No.: PCT/EP99/03918

§ 371 (c)(1),
(2), (4) Date: Dec. 11, 2000

(87) PCT Pub. No.: WO99/66001

PCT Pub. Date: Dec. 23, 1999

(30) Foreign Application Priority Data

Jun. 12, 1998 (DE) .......................... 198 26 093

(51) Int. Cl.$^7$ .............................. B32B 7/14; B32B 7/12; B32B 27/14; B32B 15/04; B05D 5/10
(52) U.S. Cl. ........................ 156/291; 428/198; 428/200; 428/343; 428/195; 427/207.1; 427/208.2; 427/208.4; 156/291; 442/149; 442/150; 442/151
(58) Field of Search ................................ 428/200, 343, 428/195, 198; 427/207.1–211; 442/150, 151, 149; 156/291

(56) References Cited

FOREIGN PATENT DOCUMENTS

| CH | 648 497 | 3/1985 | ............... C09J/7/04 |
| DE | 196 28 268 | 1/1998 | ............... C09J/7/04 |
| EP | 0 356 777 | 3/1990 | ............... C09J/7/02 |
| EP | 0 826 380 | 3/1998 | ............ A61L/15/58 |
| EP | 0 918 080 | 5/1999 | ............... C09J/7/04 |

*Primary Examiner*—Terrel Morris
*Assistant Examiner*—Lynda M Salvatore
(74) *Attorney, Agent, or Firm*—Norris McLaughlin & Marcus (57) ABSTRACT

Process for producing partially-self-adhesively treated backing materials comprising partially deformed domes or polygeometric forms of adhesive.

22 Claims, 6 Drawing Sheets

PARTIALLY SELF-ADHESIVELY TREATED ARTICLE WITH PERMANENTLY DEFORMED SELF-ADHESIVE COMPOSITION

This is a 371 of PCT/EP99/03918 filed Jun. 8, 1999 (international filing date).

The invention relates to a process for producing a partially self-adhesively treated backing material and to possible uses of the backing material obtainable by the process of the invention.

BACKGROUND OF THE INVENTION

The partial coating of backing materials with pressure-sensitive self-adhesive compositions is a known technique, whether the self-adhesive compositions are applied in patterned form, for example by screen printing (DE-C 42 37 252), in which case the domes of adhesive can also differ in their size and/or distribution (EP-C 353 972), or by intaglio printing, in lines which interconnect in the longitudinal and transverse direction (DE-C 43 08 649). In this case the preferred degree of wetting of the backing materials is from 40 to 70%.

It is also known that backing materials detachable especially without residue can be coated with self-adhesive materials.

DE-A 42 37 252 uses special geometries to achieve the absence of residue. It is entirely possible in this case to coat air-permeable backings or else film-based backings. DE-A 196 28 268 describes a self-adhesive, air-permeable and moisture-permeable sheetlike structure which has been produced in a non-continuous procedure in the form of screen printing, intaglio printing or flexographic printing. DE-A 196 28 294 describes a self-adhesive plaster which has been produced with a pressure-sensitive adhesive by screen printing, intaglio printing or flexographic printing.

In this case, the adhesive composition is applied in discrete patterns.

It is also known in the textile industry that partially coated backing materials can be transferred. EP-A 0 675 183 describes a process which transfers hotmelt pressure-sensitive adhesive geometries to a specially crosslinked substrate. A derivation for self-adhesive products is not described. The use of a coated roller as an auxiliary backing for the transfer has also already been described (CH 648 497), which again does not address self-adhesive products. The possibility of the simultaneous deliberate and permanent deformation of the discrete geometries and of the parameters which influence them, and also apparatus for realizing these parameters, is not embraced here.

DE-U 83 36 583.4 describes a pressure-sensitive adhesive sheetlike structure which can be redetached without residue.

DE-A 38 05 223 discloses a pressure-sensitive adhesive sheetlike structure with an increasing number of attachment points.

DE-A 196 20 107 describes an at least partially coated backing material where the adhesive composition is a foamed hotmelt.

DE-A 196 31 422 describes a self-adhesively treated backing material with a particularly strongly adhering hotmelt adhesive composition.

DE-A 34 33 293 discloses a self-adhesive transparent film and its process.

All of the above products and processes, respectively, have the common feature that either coating with domes is not mentioned or, if domes are applied to a backing material, these domes are not deformed.

Doping of partially coated self-adhesive tapes is also described: in U.S. Pat. No. 4,699,792, for instance, a plaster device of this kind is described, comprising active substances.

Sheetlike structures which can be redetached without residue are obtainable commercially in block form, inter alia, under the name "tesa Notes"® from Beiersdorf.

As backing materials, numerous materials on a film, woven, knit, nonwoven, gel or foam basis have already been described and are also being employed in practice.

In the medical sector, special requirements are placed on the backing materials. The materials must be compatible with the skin, generally permeable to air and/or water vapour, and also easy to model and conformable. As a result of these requirements, a very thin or soft backing is frequently preferred. For handling and in use, however, the backing materials are also required to be of sufficient strength and possibly of limited extensibility. Furthermore, the backing material should retain sufficient strength and low extensibility even after becoming wet through.

Specific applications, an example being adhesive backings for functional tape dressings for the prophylaxis and therapy of injuries, disorders and altered states of the locomotor system, require non-elastic backings having high strength in the direction of stress. This is achieved by using wovens, usually of cotton or viscose. Backing materials of this kind, particularly with appropriately high basis weight, are generally costly. High flexibility can be achieved only by means of a woven of relatively low strength. When such a fabric is stressed, however, it generally exhibits a certain degree of extension, which is undesirable for the application.

The advantage of the patterned application of the adhesive to the backing material is that the adhesive materials, given an appropriately porous backing material, are permeable to air and water vapour and, in general, are readily redetachable.

Especially in the case of medical applications, the partial application makes it possible for the transepidermal water loss to be dissipated through regulated channels, and improves the evaporation of perspiration from the skin, especially when the backing materials used are permeable to air and water vapour. This prevents skin irritations induced by instances of buildup of body fluids. The dissipation channels employed allow such fluids to be conducted away even when a multi-ply dressing is used.

A disadvantage of these products, however, is that if the area covered by the adhesive film, which is impermeable per se, is too large there is a corresponding reduction in the permeability to air and water vapour, and the consumption of adhesive composition rises, and also, if the area covered by the adhesive film is too small, the adhesion properties suffer, i.e. the product is detached too readily from the substrate, in particular from the skin, and especially in the case of heavy, textile backing materials. Permanent bonding is therefore not possible.

In the case of the pressure-sensitive self-adhesive compositions referred to, the compositions may be present in a carrier matrix for the purpose of processing. The term carrier matrix is understood to refer to common organic or inorganic solvents or dispersion media.

Systems without a carrier matrix are referred to as 100% systems and are likewise not unknown. They are processed in the elastic or thermoplastic state. A common mode of processing is that of the hotmelt.

Pressure-sensitive hotmelt adhesive compositions of this kind have also already been described in the prior art. They are based on natural or synthetic rubbers and/or other synthetic polymers.

An advantage of the 100% systems is that they avoid an operation of removing the carrier matrix, i.e. the auxiliary media, thereby raising the productivity of processing and at the same time reducing the expenditure on machinery and the energy costs. In addition, this reduces the occurrence of residues of the carrier matrix, which in turn, is to the benefit of a reduction in the allergenic potential.

The object of the invention was to provide a process for producing a partially self-adhesively treated backing material, treated on at least one side, where the backing material, owing to its treatment—i.e., to the applied form and properties of the adhesive composition and to the material properties of the backing material—serves a functionally appropriate purpose for various fixings, especially for medical products, and in doing so offers both functional and economic advantages.

SUMMARY OF THE INVENTION

The invention accordingly provides a process for producing a partially self-adhesively treated backing material, which process comprises the following steps:
a) coating a first backing material with domes and/or polygeometric structural forms of self-adhesive composition,
   a1 the add-on of the self-adhesive composition to the backing material being at least 3 g/m$^2$ and
   a2 the surface coverage of the backing material being at least 1%,
b) permanent deformation of at least some of the domes and/or polygeometric structural forms.

In particular, at least 10%, preferably 50% and, with very particular preference, 75% of the domes and/or polygeometric structural forms are permanently deformed.

Permanent deformation of all domes also constitutes a particularly preferred variant of the process of the invention. In certain cases of application, it may also be desirable for at least some of the domes to be deformed to such an extent that they flow together and form a coherent film.

It is preferred, moreover, if the domes and/or polygeometric structural forms are connected to one another at least partially by means of lines.

DETAILED DESCRIPTION

The partial deformation of the domes and/or polygeometric structural forms on the backing material makes it possible in particular to establish the desired bond strength of the backing material.

In some cases, a non-deformed fraction of domes on the backing material can also be attributed to the fact that, following deformation, some of the domes return to the original state.

The permanent deformation of the domes and/or polygeometric structural forms can take place by means of a controlled temperature regime during coating and/or by the introduction of radiative energy, mechanical energy or secondary energy.

One possibility of inducing this permanent deformation is to guide the coated backing material into a roll nip. Within the roll nip, the domes are flattened off and the base by which the domes are anchored to the backing material widens.

A partial deformation can be achieved, for example, by the use of a patterned roller in the roll nip into which the backing material is guided for the implementation of step b) of the process.

In addition, the profile of viscoelastic properties of the domes and/or polygeometric structural forms can be established by controlling the heat energy from the coating process, by the at least partial introduction of additional energy, or by the at least partial removal of heat energy, or by a combination of the techniques.

Preferably, the self-adhesive composition is applied by halftone printing, thermal screen printing or gravure printing, or by the nozzle technique, to—in particular—the first backing material.

In a preferred embodiment of the process of the invention, the application rate of the adhesive composition to the backing material is greater than 6 g/m$^2$, preferably from 20 to 1000 g/m$^2$ and with particular preference from 40 to 180 g/m$^2$.

Suitable backing materials are all rigid and elastic sheetlike structures composed of synthetic and natural raw materials. Preference is given to backing materials which, following the application of the adhesive composition, can be employed in such a way that they fulfil the characteristics of a functional dressing. Examples are textiles such as wovens, knits, lays, nonwovens, laminates, nets, films, foams and papers. In addition, these materials can be pretreated or aftertreated. Common pretreatments are corona and hydrophobicization; customary aftertreatments are calendering, thermal conditioning, laminating, punching and lining.

The backing material, especially when coated directly, must have a certain strength and density in order to prevent the domes, during their permanent deformation, from penetrating too far into the backing material or even passing right through it.

In one preferred embodiment of the process of the invention the domes and/or polygeometric structural forms are transferred to a second backing material during or after the permanent deformation. In this case the second backing material represents the actual backing, with the first backing material acting as an auxiliary backing. An auxiliary backing of this kind may also be configured in the form of an abhesively coated roller or belt.

For the coating of the backing material it is possible with advantage to employ thermoplastic hotmelt adhesive compositions based on natural and synthetic rubbers and on other synthetic polymers, such as acrylates, methacrylates, polyurethanes, polyolefins, polyvinyl derivatives, polyesters or silicones with corresponding additives such as tackifier resins, plasticizers, stabilizers and other auxiliaries where necessary.

Their softening point should be higher than 50° C., since the temperature of application is generally at least 90° C. and preferably between 100 and 150° C., or between 180 and 220° in the case of silicones. Postcrosslinking by means of UV and/or electron beam irradiation may be appropriate, if desired, in order to establish particularly advantageous properties of the hotmelt adhesive compositions.

Hotmelt adhesive compositions based on block copolymers, in particular, are notable for their diverse variation options, since the controlled reduction in the glass transition temperature of the self-adhesive composition as a result of the selection of the tackifiers, plasticizers, polymer molecule size and molecular weight distribution of the starting components ensures the required bonding to the skin in a manner appropriate to their function, even at critical points of the human locomotor system.

The high shear strength of the hotmelt adhesive composition is achieved through the high cohesiveness of the polymer. The good tack results from the range of tackifiers and plasticizers that is employed.

For systems which adhere particularly strongly, the hotmelt adhesive composition is based preferably on block copolymers, especially A-B or A-B-A block copolymers or mixtures thereof. The hard phase A is principally polystyrene or its derivatives, and the soft phase B comprises ethylene, propylene, butylene, butadiene, isoprene or mixtures thereof, particular preference being given to ethylene and butylene or their mixtures.

However, polystyrene blocks may also be present in the soft phase B, in an amount of up to 20% by weight. The overall styrene content should nevertheless always be less than 35% by weight. Preference is given to styrene contents of between 5 and 30%, since a lower styrene content makes the adhesive composition more conforming.

The controlled blending of diblock and triblock copolymers is particularly advantageous, preference being given to a diblock copolymer content of less than 80% by weight.

In one advantageous embodiment the hotmelt adhesive composition has the composition indicated below:

| | |
|---|---|
| from 10 to 90% by weight | of block copolymers, |
| from 5 to 80% by weight | of tackifiers such as oils, waxes, resins and/or mixtures thereof, preferably mixtures of resins and oils, |
| less than 60% by weight | of plasticizers, |
| less than 15% by weight | of additives, |
| less than 5% by weight | of stabilizers. |

The aliphatic or aromatic oils, waxes and resins used as tackifiers are preferably hydrocarbon oils, waxes and resins, the consistency of the oils, such as paraffinic hydrocarbon oils, or of the waxes, such as paraffinic hydrocarbon waxes, accounting for their favourable effect on bonding to the skin. Plasticizers used are medium- or long-chain fatty acids and/or their esters. These additions serve to establish the adhesion properties and the stability. If desired, further stabilizers and other auxiliaries are employed.

Filling the adhesive composition with mineral fillers, fibres or hollow or solid microbeads is possible.

Medical backing materials in particular are subject to stringent requirements in terms of the adhesion properties. For ideal application, the hotmelt adhesive composition should possess a high tack. There should be functionally appropriate bond strength to the skin and to the reverse face of the backing. So that there is no slipping, moreover, the hotmelt adhesive composition is also required to have a high shear strength. The controlled reduction in the glass transition temperature of the adhesive composition as a consequence of the selection of the tackifiers, the plasticizers, the polymer molecule size and the molecular distribution of the starting components achieves the required bonding, in a manner appropriate to the function, to the skin and to the reverse face of the backing.

The high shear strength of the adhesive composition employed here is achieved through the high cohesiveness of the block copolymer. The good tack arises from the range of tackifiers and plasticizers that is employed.

Product properties such as tack, glass transition temperature and shear stability can be quantified readily using a dynamomechanical frequency measurement. In this case, use is made of a rheometer controlled by shearing stress.

The results of this measurement method give information on the physical properties of a substance by taking into account the viscoelastic component. In this instance, at a preset temperature, the hotmelt adhesive composition is set in oscillation between two plane-parallel plates with variable frequencies and low deformation (linear viscoelastic region). Via a pickup control unit, with computer assistance, the quotient (Q=tan δ) between the loss modulus (G", viscous component) and the storage modulus (G', elastic component) is measured.

$$Q = \tan \delta = G''/G'$$

A high frequency is chosen for the subjective sensing of the tack and a low frequency for the shear strength.

A high numerical value denotes better tack and poorer shear stability.

The glass transition temperature is that temperature at which amorphous or partially crystalline polymers undergo transition from the liquid or rubber-elastic state into the hard-elastic or glassy state, or vice versa (Römpp Chemie-Lexikon, 9th ed., volume 2, page 1587, Georg Thieme Verlag Stuttgart—New York, 1990). It corresponds to the maximum of the temperature function at a predetermined frequency.

For medical applications in particular, a relatively low glass transition point is required.

| Designation | $T_g$ low frequency | Conformability low frequency/RT | Tack high frequency/RT |
|---|---|---|---|
| Hotmelt adhesive composition A | −12 ± 2° C. | tan δ = 0.32 ± 0.03 | tan δ = 1.84 ± 0.03 |
| Hotmelt adhesive composition B | −9 ± 2° C. | tan δ = 0.22 ± 0.03 | tan δ = 1.00 ± 0.03 |

The hotmelt adhesive compositions are preferably formulated such that their dynamic-complex glass transition temperature at a frequency of 0.1 rad/s is less than 15° C., preferably from 5 to −30° C. and, with very particular preference, from −3 to −15° C.

In accordance with the invention, preference is given to hotmelt adhesive compositions for which the ratio of the viscous component to the elastic component at a frequency of 100 rad/s at 25° C. is greater than 0.7, in particular between 1.0 and 5.0, or to hotmelt adhesive compositions for which the ratio of the viscous component to the elastic component at a frequency of 0.1 rad/s at 25° C. is less than 0.6, preferably between 0.4 and 0.02 and, with very particular preference, between 0.35 and 0.1.

Preferably, the domes and/or polygeometric structural forms applied to the first backing material possess, at the time of deformation, a plasticity/elasticity ratio of greater than 0.3 to 50 at a frequency of 100 radical/s.

The domes or polygeometric structural forms can have various shapes. Flattened hemispheres are preferred. Printed application of other shapes and patterns on the backing material is also possible—for example, a printed image in the form of alphanumeric character combinations or patterns such as matricies, stripes, assemblies of domes, and zig-zag lines.

In addition, for example, the composition can be applied by spraying, so producing a more or less irregular application pattern.

The adhesive composition can be distributed uniformly over the backing material; alternatively, it can be applied with a thickness or density which varies over the area, as appropriate for the function of the product.

The process of the invention for coating the backing material achieves a saving on adhesive composition in comparison to a conventional partially coated backing material, for a given contact area with the substrate, and greater adhesion to the substrate for a given applied weight of adhesive composition.

At the same time there is substantially no adverse effect on the advantageous, high permeability of the adhesive film for air and water vapour for special applications, especially in the medical sector.

The particularly preferred process for producing the self-adhesively treated backing material described features a total of three steps:

In the first step, the geometric structures formed from hotmelt adhesive composition are applied by means of halftone printing, thermal screen printing or intaglio printing, or by the nozzle process to a carrier; in the second step, the carrier together with the structures is guided on to the backing material; and, finally, the structures are permanently deformed and transferred from the carrier to the backing material.

The term carriers is to be understood as meaning conventional, continuous webs of various materials, but also means such as rollers and transfer tapes.

The first backing material preferably has a surface with a random or regular three-dimensional geometric structure.

By means of a random or regular three-dimensional geometric structure of the auxiliary backing, such as a particular surface roughness or surface shaping, for example, further influence may be exerted on the resulting geometry of the permanently deformed hotmelt pressure-sensitive adhesive domes.

A preferred embodiment of the auxiliary backing is the roller with an abhesive surface, it being possible for the abhesive surface of the roller to comprise silicones or fluorine compounds or a plasma-coated release system. These may be applied in the form of a coating having a weight per unit area of from 0.001 $g/m^2$ to 3000 $g/m^2$, preferably from 100 to 2000 $g/m^2$.

For the implementation of the process it is desirable for the abhesive surface of the roller to be adjustable in its temperature between 0° C. and 200° C., preferably less than 60° C., with particular preference less than 25° C. In this context it is particularly advantageous if the abhesive properties of the surface of the roller are matched so that the applied self-adhesive composition adheres even to a cooled roller (<25° C.).

In order to prevent excessive wear of the roller or of a coating apparatus in contact with it, it is sensible to match the elasticities of these two components to one another. It has proven to be advantageous for the elasticity of the surface of the roller to be located within the rubber-elastic range.

The transfer of the self-adhesive composition from the roller to the second backing material may be initiated via a pickup roller which is guided against the roller. Permanent deformation of the adhesive geometries may follow this. Preferably, however, the shaping of the domes takes place simultaneously with the transfer, so removing the need for a separate deformation apparatus. For this purpose it is advantageous to be able to position the pickup roller precisely in the radial direction, and preferably also in the peripheral direction, with respect to the abhesive roller. Alternatively to the radial position, it is also possible to define a pressing force. Using these adjustment devices it is possible to influence not only the temperature regime but also the degree of permanent deformation.

One particularly preferred process for transferring the hotmelt pressure-sensitive adhesive from the abhesive roller to the second backing material uses a pair of deflection devices which is arranged at different positions along the periphery of the abhesive roller, the second backing material being guided a distance along the surface of the abhesive roller.

Preferred deflection devices are rollers.

This process is particularly advantageous in cooperation with the cooling of the abhesive roller, since following deformation and transfer of the domes to roller, which for this purpose should be parameterable as elucidated above for roller, the material covers a cooling section on the roller and it is therefore possible to prevent cohesive fracture of the hotmelt pressure-sensitive adhesive on detachment from the abhesive surface of the roller.

Depending on the backing material and its temperature sensitivity, however, the hotmelt adhesive composition can also be applied directly to the backing material.

Subsequent calendering of the coated product and/or pretreatment of the backing, such as corona irradiation, may also be advantageous for better anchoring of the adhesive film.

In addition, treatment of the hotmelt adhesive composition by electron beam post crosslinking or by UV radiation may result in an improvement in the desired properties.

The principle of thermal screen printing consists in the use of a rotating, heated, seamless, drum-shaped, perforated, cylindrical screen which is fed via a nozzle with the preferred hotmelt adhesive composition. A specially shaped nozzle lip (circular or square-section coating bar) presses the hotmelt adhesive composition, which is fed in via a channel, through the perforation of the screen wall and on to the backing web that is conveyed past it. This backing web is guided by means of a counter-roller against the external jacket of the heated screen drum at a rate which corresponds to the peripheral speed of the rotating screen drum.

In this process, the small domes of adhesive are formed in accordance with the following mechanism:

The pressure of the nozzle coating bar conveys the hotmelt adhesive composition through the screen perforation on to the backing material. The size of the domes formed is predetermined by the diameter of the screen perforation. The screen is lifted from the backing in accordance with the rate of transportation of the backing web (rotary speed of the screen drum). As a consequence of the high adhesion of the adhesive composition and of the internal cohesion of the hotmelt, the limited supply of hotmelt adhesive composition in the perforations is drawn in sharp definition from the base of the domes, which is already adhering to the backing, and is conveyed on to the backing by the pressure of the coating bar.

Following the end of this transportation, the more or less highly curved surface of the dome forms over the predefined base area in dependence on the rheology of the hotmelt adhesive composition. The height-to-base ratio of the dome depends on the ratio of the perforation diameter to the wall thickness of the screen drum and on the physical properties (rheology, surface tension and contact angle on the backing material) of the self-adhesive composition.

For the screen in thermal screen printing, the web-to-hole ratio can be less than 10:1, preferably less than or equal to 1:1 and, in particular, equal to 1:3.

The above-described mechanism of formation of the domes requires, preferentially, backing materials that are absorbent or at least wettable by hotmelt adhesive composition. Non-wetting backing surfaces must be pretreated by chemical or physical methods. This can be done by means of additional measures such as corona discharge, for example, or by coating with substances which improve wetting.

Using the printing technique indicated it is possible to lay down the size and shape of the domes in a defined manner. The bond strength values which are relevant for use, e.g. those which determine the quality of the products formed, are within very narrow tolerances provided that coating is carried out correctly. The base diameter of the domes can be chosen to be from 10 to 5000 µm, the height of the domes from 20 to 2000 µm, preferably from 50 to 1000 µm, the low-diameter range being intended for smooth backings and the range of greater diameter and greater dome height being intended for rough or highly porous backing materials.

The positioning of the domes on the backing is laid down in a defined manner by the geometry of the applicator unit, for example the gravure or screen geometry, which can be varied within wide limits. With the aid of the parameters indicated it is possible, by way of adjustable variables, to establish with very great precision the desired profile of properties of the coating, tailored to the various backing materials and applications.

The backing material is preferably coated at a rate of more than 2 m/min, preferably from 20 to 200 m/min, the coating temperature being chosen to be greater than the softening temperature.

The percentage area that is coated with the hot melt adhesive composition should be at least 1% and can be up to approximately 99%, for specific products preferably from 15 to 95% and, with particular preference, from 50 to 95%. This can be achieved, if desired, by means of multiple application, in which case even hotmelt adhesive compositions having different properties can be employed if desired.

A controlled temperature regime and/or the introduction of radiative energy, mechanical energy or secondary energy during production make it possible in the case of thermoplastic self-adhesive compositions to modify the geometry of the geometric structures, it being possible to vary the base diameters within wide limits. Preferably, a controlled temperature regime can also be operated for the thermoplastic or elastic primary domes, i.e. the domes applied to the carrier, this regime being brought about, for example, by radiative heating, such as IR, by means of which it is possible to generate secondary domes having the optimum bonding properties for dome transfer.

Energy control in the material and/or at the surface of the polymers permits a great diversity of polygeometric dome forms. For the ultimate shaping of the transferred secondary dome, it may be advantageous to have a regulatable printing station (gap/pressure/temperature/speed). Subsequent calendering may also be advantage The profile of viscoelastic properties which is present, prior to the transfer of the secondary dome, in the structures formed from self-adhesive composition can be adjusted by controlling the heat energy from the coating process, by the at least partial introduction of surface energy, or by the at least partial removal of heat energy, or by a combination of the techniques.

The geometric structures can, accordingly, be divided into a plurality of zones which may have entirely different characteristics. The geometric structures applied to the carrier, at the time of transfer to the backing material, preferably have, in the base zone, which corresponds to that part of the structure which lies against the backing material, a plasticity/elasticity ratio at a frequency of 100 rad/s of from 0.3 to 50.

The combination of the hotmelt adhesive composition and the partial coating ensures secure bonding of the backing material.

Especially if the backing material is used to produce a medical product, this product adheres to the skin and, on the other hand, allergic or mechanical skin irritations—at least those which are visually discernable—are prevented, even in the case of an application which extends over several days.

Partial application makes it possible, through controlled channels, to dissipate the transepidermal water loss, and improves the removal of perspiration from the skin in vapour form, especially when the backing materials used are permeable to air and water vapour. By this means, skin irritations induced by accumulation of body fluids are prevented. The dissipation channels that have been set up enable fluids to be conducted away, even when a multi-ply dressing is used.

In a further preferred embodiment of the process of the invention, the coated backing material has an air permeability of more than 1 $cm^3/(cm^{2+}$ s), preferably from 10 to 150 $cm^3/(cm^{2+}$ s), and/or a water vapour permeability of more than 200 $g/(m^{2+}24$ h), preferably from 500 to 5000 $g/(m^{2+}24$ h).

In a further preferred embodiment of the process of the invention, the backing material on steel has a bond strength to the reverse face of the backing of at least 0.5 N/cm, in particular a bond strength of between 2 N/cm and 12 N/cm.

The epilation of corresponding body regions and the transfer of composition to the skin are negligible, owing to the high cohesiveness of the adhesive, since the adhesive is not anchored to skin and hair; rather, the anchoring of the adhesive composition to the backing material, at up to 12 N/cm (sample width), is good for medical applications.

Because of the intended-breakage points that have been formed in the coating, layers of skin are no longer displaced with one another or against one another in the course of detachment. The non-displacement of the layers of skin and the relatively low level of epilation lead to an unprecedented degree of painlessness in such strongly adhering systems. In addition, the individual biomechanical control of bond strength, which exhibits a demonstrable reduction in the bond strength of these plasters, assists detachability. The applied backing material shows good proprioceptive effects.

In a further advantageous embodiment, the self-adhesive compositions are foamed before being applied to the backing material.

In this case, the self-adhesive compositions are preferably foamed using inert gases, such as nitrogen, carbon dioxide, noble gases, hydrocarbons or air, or mixtures thereof. In some cases, foaming additionally by thermal decomposition of gas-evolving substances, such as azo, carbonate and hydrazide compounds, has been found suitable.

The degree of foaming, i.e. the gas content, should be at least about 5% by volume and can reach up to about 85% by volume. In practice, levels of from 10 to 75% by volume, preferably 50% by volume, have been found appropriate. Operating at relatively high temperatures of approximately 100° C. and with a comparatively high internal pressure, produces very open-pored adhesive foam layers which are particularly permeable to air and water vapour.

The advantageous properties of the foamed self-adhesive coatings, such as low consumption of adhesive, high tack and good conformability, even on uneven surfaces, owing to the elasticity and plasticity, and also the initial tack, can be utilized to best effect in the field of medical products.

The use of breathable coatings in conjunction with elastic and likewise breathable backing materials produces a level of wear comfort which is perceived subjectively by the user as being more pleasant.

A particularly suitable process for producing the foamed self-adhesive composition operates in accordance with the foam mixing system. Here, the thermoplastic self-adhesive composition is reacted under high pressure with the intended gases, such as nitrogen, air or carbon dioxide, for example, in various proportions by volume (from about 10 to 80% by volume) in a stator/rotor system and at a temperature above the softening point (approximately 120° C.).

While the gas entry pressure is greater than 100 bar, the mixing pressures between gas and thermoplastic in the system are from 40 to 100 bar, preferably from 40 to 70 bar. The pressure-sensitive adhesive foam produced in this way can subsequently be passed through a line into the applicator unit. In the applicator unit, commercially customary nozzles, extruder systems or chamber systems are used.

By virtue of the foaming of the self-adhesive composition and of the open pores in the composition which form as a result, and given the use of an inherently porous backing, the products coated with the adhesive composition have good permeability to water vapour and air. The amount of adhesive composition required is reduced considerably without any adverse effect on the adhesion properties. The adhesive compositions have a surprisingly good tack, since per gram of composition there is more volume and thus more adhesion surface for wetting of the substrate that is to be bonded, and the plasticity of the adhesive compositions is increased by the foam structure. Anchoring to the backing material is also improved in this way. The foamed adhesive coating, moreover, as has been mentioned above, gives the products a soft and smooth feel.

Foaming also reduces the viscosity, in general, of the adhesive compositions. This lowers the melt energy, and even thermally unstable backing materials can be coated directly.

The outstanding properties of the self-adhesively treated backing material of the invention suggest its use for medical products, especially plasters, medical fixings, wound coverings, doped systems especially those which release substances, and for orthopaedic or phlebological bandages and dressings.

Finally, following the coating operation, the backing material can be lined with an anti-adhesive backing material, such as siliconized paper, or can be provided with a wound pad or padding.

It is particularly advantageous if the backing material can be sterilized, preferably by means of γ-(gamma) radiation. Consequently, particular suitability for subsequent sterilization is possessed by block copolymer-based hotmelt adhesive compositions which contain no double bonds. This applies in particular to styrene-butylene-ethylene-styrene block copolymers or styrene-butylene-styrene block copolymers. In this case, the adhesive properties are not subject to any changes significant for the application.

The backing materials are also outstandingly suited to industrial reversible fixings which on removal cause no damage or injury to a variety of substrates, such as paper, plastics, glass, textiles, wood, metals and minerals.

Finally, it is possible to produce technically permanent bonds which can be separated only with partial splitting of the substrate.

BRIEF DESCRIPTION OF THE DRAWINGS

With reference to a number of figures, advantageous embodiments of the subject-matter of the invention will now be described, without wishing thereby unnecessarily to restrict the invention.

Of these figures.

Figure 1:
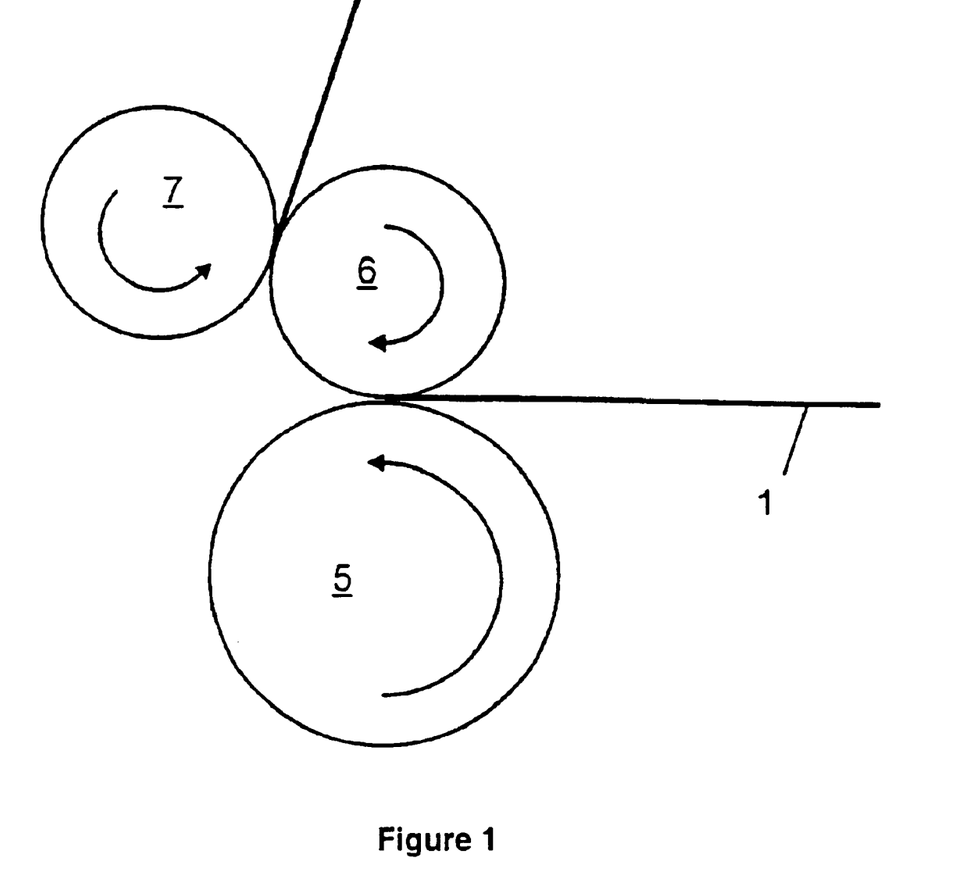
FIG. 1 shows a section of a unit which operates in accordance with the process of the invention.

FIG. 1 shows a section of a unit which operates in accordance with the process of the invention. The backing material 1 is guided into a nip between the screen roller 5 and the counterpressure roller 6. The backing material 1 is coated by the screen roller 5 with domes comprising a hotmelt adhesive composition.

After the backing material 1 has been coated it is guided into a further roll nip formed by the counterpressure roller 6 and a pressure roller 7. Within the roll nip there is a permanent deformation of the domes applied to the backing material 1.

Figure 2:
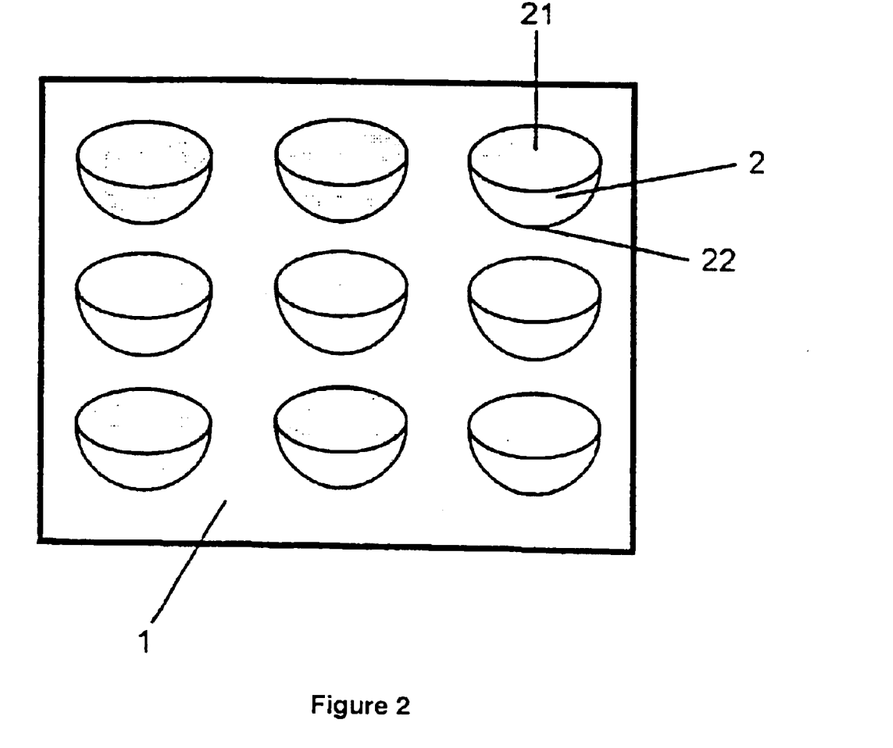
FIG. 2 shows a backing material coated with hemispherical domes.

FIG. 2 shows a section taken from a continuous backing material 1 which is coated with essentially hemispherical domes 2. Within each individual dome 2 it is possible to make out a base zone 22, which lies in that region of the dome 2 in which the dome 2 is anchored to the backing material 1, and the head zone 21, which is opposite to the base zone 22. Both zones 21 and 22 can, if desired, have characteristics which deviate from one another.

Figure 3:
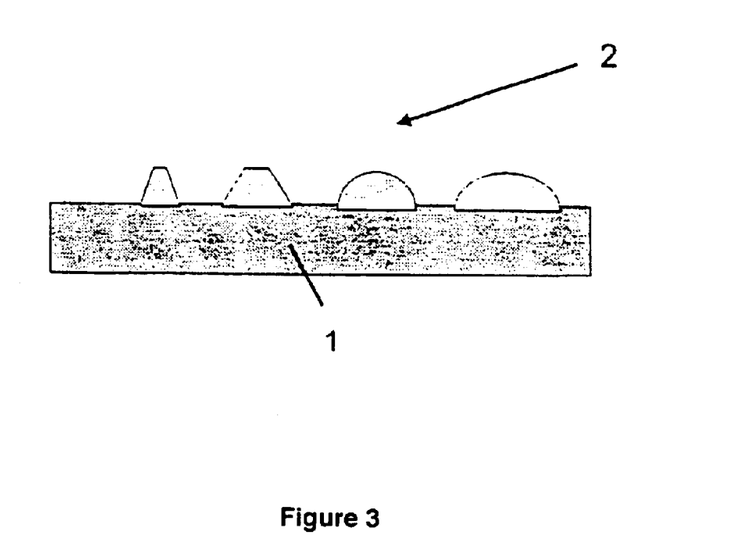
FIG. 3 shows a backing material coated in lateral section with differently shaped domes (configuration for reversible bonding)
Figure 4:
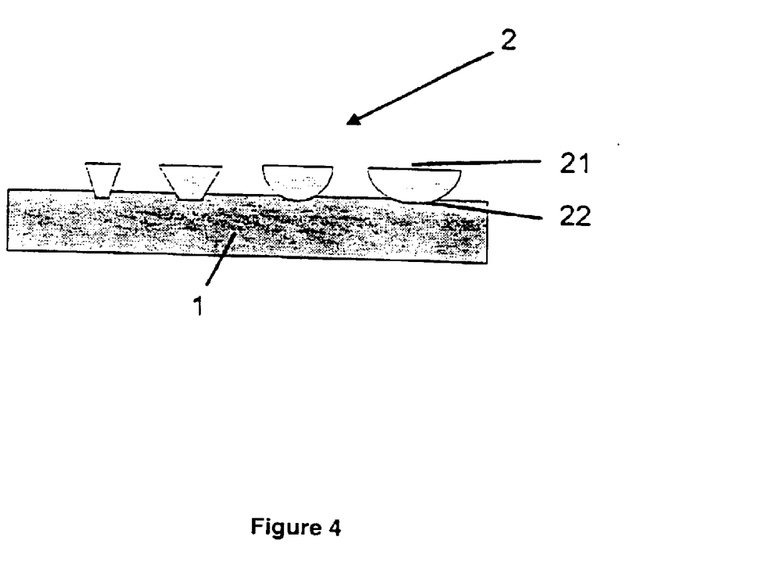
FIG. 4 shows a backing material coated in lateral section with differently shaped domes (configuration for permanent bonding)

FIGS. 3 and 4, finally, show differently shaped domes 2 in lateral section which have been found particularly advantageous.

In the case of FIG. 3, a backing material 1 is shown which by virtue of the formation of the domes 2 has a reversible adhesive configuration, i.e. following application to the skin the backing material 1 can be removed without problems and used for bonding again.

In the case of FIG. 4, a backing material 1 is shown which by virtue of the formation of the domes 2 has an irreversible adhesive configuration, i.e. following application to the skin the backing material 1 cannot be removed without problems; instead, it adheres to the skin with particular strength.

Figure 5:
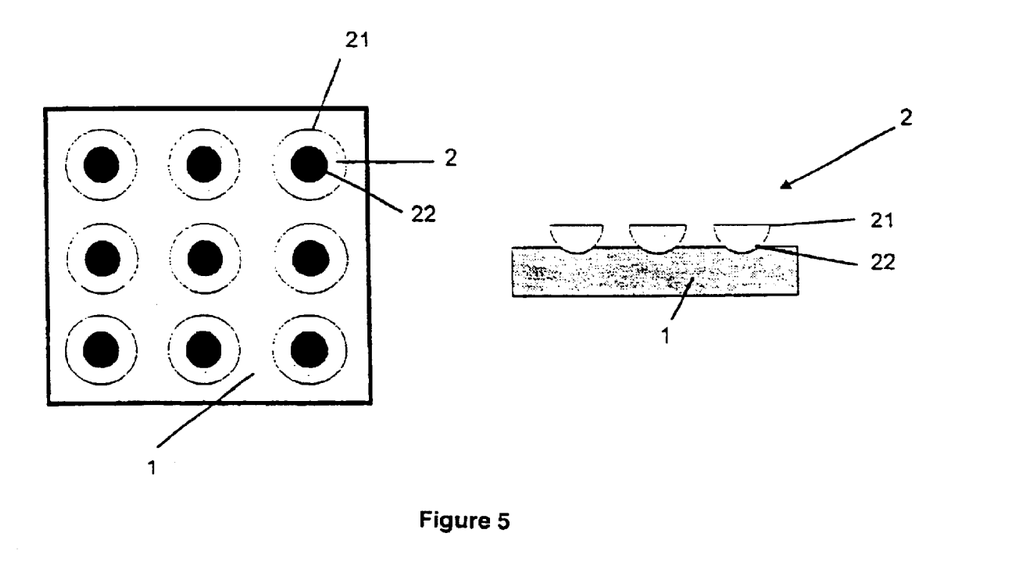
FIG. 5 shows a backing material coated with hemispherical domes in plan view and in side elevation prior to the permanent deformation of the domes.

In FIG. 5, a backing material 1 coated with hemispherical domes 2 is shown in plan view and in side elevation prior to the permanent deformation of the domes 2.

Figure 6:
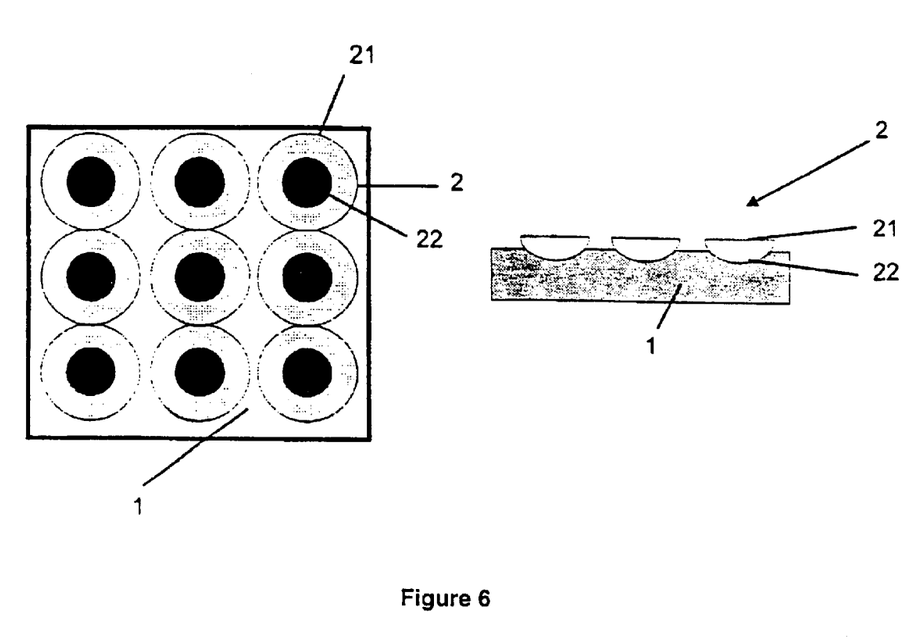
FIG. 6 shows a backing material coated with hemispherical domes in plan view and in side elevation after the permanent deformation of the domes.

In FIG. 6, a backing material 1 coated with hemispherical domes 2 is shown in plan view and in side elevation after the permanent deformation of the domes 2. The height of the domes 2 has reduced considerably, and at the same time the area of the head zone 21 has become larger. The base zone 22 has also become larger relative to the non-deformed domes 2. Then, overall, the domes 2 have penetrated a little deeper into the backing material 1. Initial lines are formed in part between the domes 2.

Figure 7:
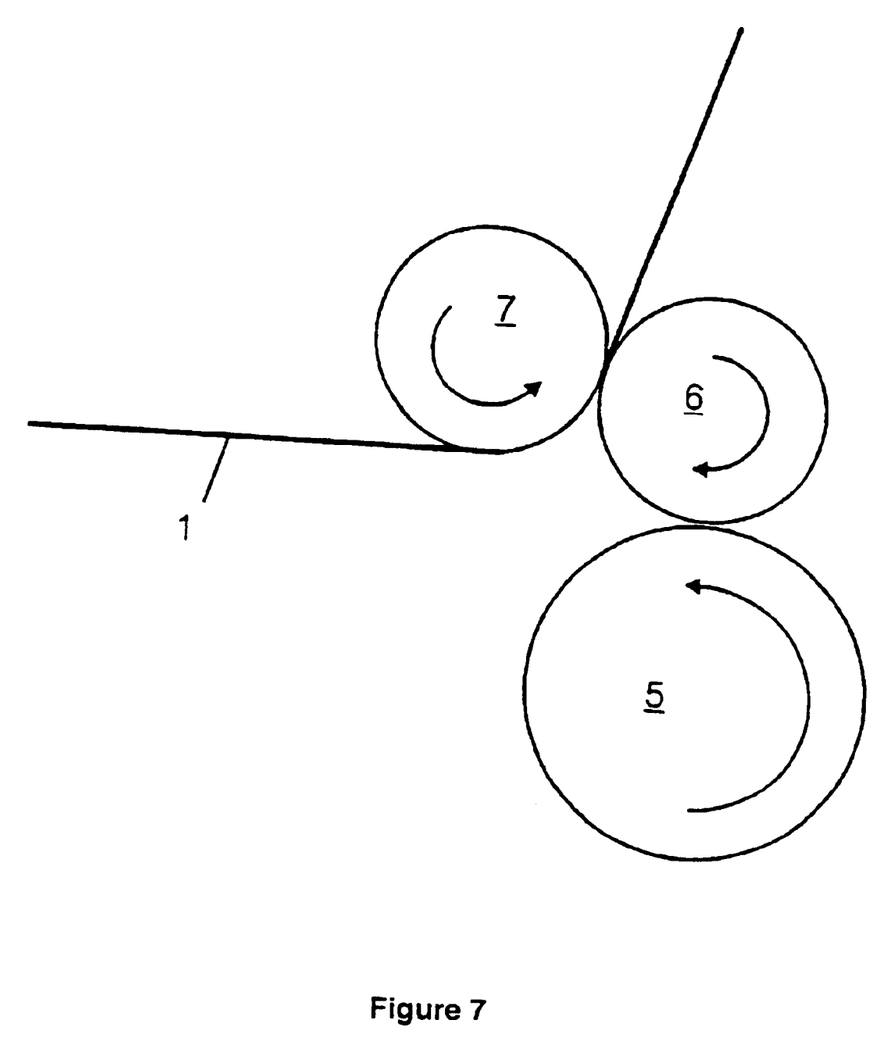
FIG. 7 shows a section of plant when using an abhesive counterpressure roller (6) as auxiliary backing.

In FIG. 7, the section of plant when using an abhesive counterpressure roller (6) as auxiliary backing is depicted. The hotmelt adhesive composition is picked up from the counterpressure roller on a line by means of the backing material guided around the pressure roller (7), and at the same time the pressure roller performs the permanent deformation.

Figure 8:
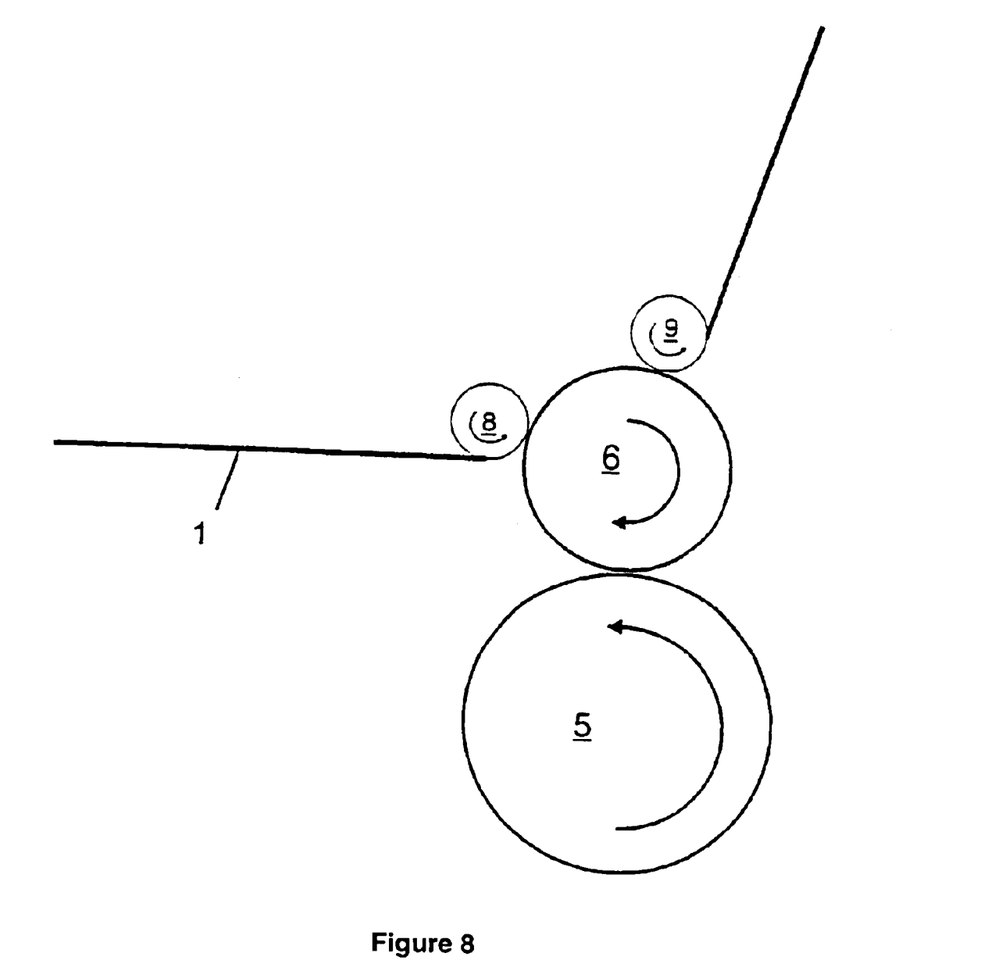
FIG. 8 shows the use of an abhesive counterpressure roller with a roller pair for deformation and for transfer of the hotmelt adhesive composition.

FIG. 8 shows the preferred embodiment of the use of an abhesive counterpressure roller (6) having a roller pair (8,9) for deformation and for transfer of the hotmelt adhesive composition.

In the text below, a backing material of the invention which has been given a self-adhesive treatment is illustrated by means of an example, again without wishing unnecessarily to restrict the invention.

EXAMPLE 1

In accordance with the invention, a non-elastic self-adhesive bandage was produced which, owing to its properties, described below, can be used as a functional tape dressing, the functional dressing technique being guided by the anatomy and the biomechanics.

The bandage used for this type of dressing consisted of a non-elastic woven cotton fabric with a breaking strength of more than 60 N/cm and a breaking extension of less than 20%.

The self-adhesive composition was applied by thermal screen printing, and was a hotmelt adhesive having the following composition:

a A-B/A-B-A block copolymer consisting of hard and soft segments, with a ratio of A-B-A to A-B of 2:1 and a styrene content in the polymer of 13 mol %; its proportion in the adhesive composition is 40% by weight (Kraton G)

a paraffinic hydrocarbon wax whose proportion in the adhesive composition is 45% by weight hydrocarbon resins with a proportion of 14.5% by weight (Super Resin HC 140)

an ageing inhibitor with a proportion of less than 0.5% by weight (Irganox).

The components employed were homogenized in a thermal mixer at 195° C.

The softening point of this adhesive composition was about 85° C. (DIN 52011), and the adhesive composition had a viscosity of 2100 mPas at 150° C. (DIN 53018, Brookfield DV II, sp. 21). The glass transition temperature according to the method set out above was −7° C.

The pressure-sensitive adhesive geometry of the invention was realized by means of the above-described transfer of the domes of pressure-sensitive adhesive composition from a carrier on to the backing material:

The indirect coating took place at 15 m/min and at a temperature of 120° C. on to a release paper (carrier) and from there on to the backing material.

Shortly before the backing material was introduced, energy was supplied by irradiation of the adhesive composition. This led to a gradient of the dome of adhesive composition adhering to the carrier in a zone of high plasticity and low elasticity and a base zone of low plasticity and high elasticity. A transition zone was established in between.

Under pressurized transfer on to the textile backing material, the low-viscosity head zone penetrated readily into the backing material, where it provided good anchoring of the dome of adhesive composition; the high-viscosity zone laid itself on to the backing material and controls the adhesive properties of the products.

By means of suitable pressure control in the transfer nips it is possible to establish the degree of deformation of the highly viscose zone with precision. Deformation can be carried out until a full-area coating pattern is obtained.

With a subsequent backing material thickness (backing+ adhesive composition) of 0.35 mm, the laminating gap used in the example is 0.95 mm. This is therefore not a known calendering process, where the nip dimension, owing to the elastic effects, is less than the thickness of the calendered backing material, but instead is a kind of spreading of the domes under the action of the laminating nip and the web tension, for which the above-described, exact establishment of the viscoelastic profile of properties of the dome is an absolute prerequisite.

It has been found advantageous to bring the entire pressure-sensitive hotmelt adhesive domes, before transfer, into the desired viscoelastic state of the base zone or to obtain this state from the heat of fusion.

The backing material was coated with 120 g/m$^2$, using a 14 mesh HX screen stencil.

Owing to the transfer from the smooth carrier, moreover, the surface of the adhesive composition acquired a planar surface which was likewise suitable for enlarging the contact area with planar substrates.

The bond strength to the reverse face of the backing was from 30 to 50% greater than that of a comparison sample without dome deformation but with the same mass add-on.

The bandage produced in accordance with this process exhibited reversible detachment from the skin and good permeability to air and water vapour. Because of the high shear stability of the hotmelt pressure-sensitive adhesive, sufficient stabilization and a good proprioreceptive effect were found. No skin irritation was observed after the bandage had been taken off.

What is claimed is:

1. Process for producing a partially self-adhesively treated backing material, comprising the following steps:
    a) coating a first backing material with a self-adhesive composition in the form of a plurality of individual, discrete domes, or a plurality of individual, discrete polygeometric structural forms, or both, the add-on of the self-adhesive composition to the backing material being at least 3 g/m$^2$ and the surface coverage of the backing material being at least 1%,
    b) deforming at least some of the domes, polygeometric structural forms or at least some of each sufficiently to cause them to contact and become attached to other domes, or polygeometric forms or both, while substantially retaining the character of all of said domes and polygeometric forms as individual, discrete domes or polygeometric shapes.

2. Process according to claim 1, wherein at least 10% of the domes, polygeometric structural forms or of both of them are deformed.

3. Process according to claim 1, wherein deformation of the domes or polygeometric structural forms takes place by means of a controlled temperature regime during coating or by the introduction of radiative energy, mechanical energy, or by a combination thereof.

4. Process according to claim 1, wherein the self-adhesive composition is applied to the first backing material by halftone printing, thermal screen printing or gravure printing or by a spraying process.

5. Process according to claim 1, wherein the add-on of the self-adhesive composition to the first backing material is greater than 6 g/m$^2$.

6. Process according to claim 1, wherein the first backing material is a roller (6) or a belt, with an abhesive surface, the abhesive surface comprising a coating of silicones or fluorine compounds or a plasma-coated release system, which is applied with a weight per unit area of from 0.001 g/m² to 3000 g/m².

7. Process according to claim 6, wherein said first backing material is a roller, the surface-temperature of which is adjustable and the abhesive properties of the surface are such that the applied self-adhesive composition adheres to the surface of the roller.

8. Process according to claim 1, wherein the domes and/or polygeometric structural forms are transferred to a second backing material during or after the deformation.

9. Process according to claim 6, wherein the domes, polygeometric structure forms or both are transferred to a second backing material during or after the deformation, by guiding the second backing material against the abhesive surface of the roller (6) or of the belt by way of a pickup roller (7) which is positionable in the peripheral direction and/or radial direction with respect to the roller or to the belt and/or may force the second backing material against the domes, polygeometric forms or both, with pressure, so that the degree of deformation may be influenced.

10. Process according to claim 8, wherein the transfer of the self-adhesive composition takes place by means of a pair of deflection devices (8, 9) which is arranged at different positions along the periphery of the abhesive roller (6) or of the belt, the second backing material being guided a distance along the surface of the abhesive roller (6) or the belt.

11. Process according to claim 10, wherein the deflection devices (8, 9) comprise rollers which are positionable in the peripheral direction, radial direction or both with respect to the roller (6) or belt and which optionally force the second backing material against the domes, polygeometric forms or both, with pressure, so that the degree of deformation is optionally influenced.

12. Process according to claim 1, wherein the first backing material has a surface which has a random or regular three-dimensional geometric structure.

13. Process according to claim 1, wherein the self-adhesive composition is a hotmelt adhesive composition.

14. Process according to claim 1, wherein the viscoelastic properties of the domes, polygeometric structural forms or of both are established by controlling the heat energy from the coating process, by the at least partial introduction of additional energy, or by the at least partial removal of heat energy, or by a combination thereof.

15. Process according to claim 1, wherein the domes, polygeometric structural forms or both applied to the backing material have a plasticity/elasticity ratio at the time of deformation, at a frequency of 100 rad/s, of greater than 0.3 to 50.

16. Process according to claim 13, wherein the hotmelt adhesive composition is in foamed form, and is optionally crosslinked by means of electron beams, UV or both.

17. Process according to claim 1, wherein the side of the backing material opposite the adhesive has a bond strength to steel of at least 0.5 N/cm.

18. Plasters, medical adhesive tapes, wound coverings, doped systems, and orthopaedical and phlebological bandages and dressings comprising partially self-adhesively treated backing materials prepared according to claim 1.

19. Plasters, medical adhesive tapes, wound coverings, doped systems and orthopaedical and phlebological bandages and dressing according to claim 18, wherein following its production, the partially self-adhesively treated backing material is lined or provided with a wound pad or padding and/or is sterilized.

20. Industrial and reversible adhesive tapes comprising the partially self-adhesively treated backings prepared according to claim 1, which on removal cause no damage or injury to substances of paper, plastics, glass, textiles, wood, metals or minerals.

21. A method for forming bonds which can be separated only with partial splitting of the substrate which comprises forming said bonds with partially self-adhesively treated backing materials prepared according to claim 1.

22. The process of claim 19, wherein said backing material is sterilized by γ(gamma) radiation.

* * * * *